United States Patent [19]

Kaminsky

[11] Patent Number: 5,093,104

[45] Date of Patent: Mar. 3, 1992

[54] METHOD FOR LABELLING LEUCOCYTES WITH INDIUM IN-111 OXINE

[75] Inventor: Deborah Kaminsky, Overland Park, Kans.

[73] Assignee: Syncor International Corporation, Chatsworth, Calif.

[21] Appl. No.: 395,353

[22] Filed: Aug. 17, 1989

[51] Int. Cl.⁵ ............................................. A61K 39/395
[52] U.S. Cl. ..................................... 424/1.1; 530/380; 530/402
[58] Field of Search .................. 424/1.1; 530/380, 402

[56] References Cited

PUBLICATIONS

H. J. Danpure et al., Nuclear Medicine Communications (1988), vol. 9, pp. 681–685.
Operating Instructions for a "Hema Tek" Aliquot Mixer from Miles Laboratories, Inc.

*Primary Examiner*—John S. Maples
*Attorney, Agent, or Firm*—Donald G. Lewis

[57] ABSTRACT

An improved method for radio-labelling leucocytes in vitro with Indium In-111 oxide (Indium In-111 oxyquinoline) for use in scintigraphic imaging of inflammatory lesions and abscesses enhances the leucocyte specific labelling efficiency by depleting residual RBCs from the leucocytes prior to labelling. The RBCs are depleted from the leucocytes by means of a rocking step.

2 Claims, No Drawings

METHOD FOR LABELLING LEUCOCYTES WITH INDIUM IN-111 OXINE

The invention relates to methods for radiolabelling leucocytes in vitro with gamma-emitting radionuclides. The radiolabelled leucocytes are employed for imaging inflammatory lesions by scintigraphy after injection into a patient. More particularly, the invention relates to methods for enhancing the efficiency of leucocyte specific labelling in vitro by Indium In-111 oxine (oxyquinoline) while maintaining sterility and viability.

BACKGROUND

Methods for radiolabelling human leucocytes with gamma emitters have been reviewed by H. J. Danpure and S. Osman ("A Review of Methods of Separation and Radiolabelling Human Leucocytes,"Nuclear Medicine Communications (1988); vol. 9, 681–685). Danpure and Osman indicate that successful radiolabelling methods employ neutral lipophilic agents which chelate the selected gamma emitting radionuclide and carry the radionuclide across the cellular memebrane into the patient's or donor's isolated leucocytes. Once inside the leucocyte, the lipophilic chelator may be degraded or otherwise modified so as to produce a hydrophilic radionuclide product. The hydrophilic radionuclide product remains entrapped within the leucocytes for a period sufficiently long to allow rapid injection of the labelled leucocytes into the patient, migration of the labelled leucocytes to inflamation sites, and scintigraphic imaging of inflamation sites by means of the labelled leucocytes. Danpure and Osman indicate that the gamma-emitting radionuclide Indium In-111 oxine has been successfully employed in clinical settings for radiolabelling mixed leucocytes for scintigraphic imaging.

Prior art methods for Indium In-111 labelling can yield an overall labelling efficiency of approximately 99%. However, the labelled leucocyte product is significantly contaminated with labelled red blood cells (RBCs). If labelled granulocytes are sparated from the mixed leucocytes by density gradient according to the method of Danpure (supra), it is found that approximately 85-95% of the Indium In-111 label is incorporated by the granulocytes and approximately 5-15% of the Indium In-111 label is incorporated by RBCs. Hence, the leucocyte specific labelling efficiency is significantly less than 99%. This less than optimal labelling efficiency results in product impurities, e.g. Indium In-111 labelled RBCs, which adds unnecessary radioactive contamanents to the leucocyte product. Also, a loss of Indium In-111 adds to the overall cost.

Contamination of the labelled leucocyte product by labelled RBCs is undesirable because it exposes the patient to a higher than necessary dosage of Indium In-111. Furthermore, under certain conditions, the contaminant RBCs detract from the resolution of the scintigraphic imaging. Labelled RBCs circulate and create diffuse background uptake. Labelled RBCs which are damaged tend to collect preferentially in the spleen and liver. Consequently, colonic and other abdominal abscesses may be difficult to image. Gamma emissions from labelled RBCs which have preferentially collected in the spleen and liver may interfer scintigraphically with the imaging of colonic or other abdominal abscesses to which labelled leucocytes have migrated.

Since Indium In-111 is a low gamma emitter, a comparatively elevated dosage of Indium In-111 is required for effective scintigraphic imaging. However, under many circumstances, the Food and Drug Administration (FDA) restricts the dosage to 500 microcuries. In order to achieve good imaging, it is standard medical procedure to administer the highest dosage allowed by the FDA. Accordingly, image enhancement by the use of increased label is usually not an available option.

What is required is a method for labelling leucocytes with Indium In-111 which results in a high leucocyte specific labelling efficiency. The labelled leucocyte product should have substantially no contamination of Indium In-111 labelled RBCs.

SUMMARY

The efficiency of leucocyte specific labelling using Indium In-111 oxine may be significantly enhanced and contamination of the labelled leucocyte product by labelled RBCs may be significantly reduced by depleting residual RBCs from the leucocytes prior to the labelling step.

DETAILED DESCRIPTION OF THE INVENTION

A preferred protocol for high efficiency labelling of leucocytes with Indium In-111 oxine is provided as follows:

1. A blood sample is drawn from the patient using a 60 milliliter syringe. Prior to drawing the blood sample, an aliquot of 1000-2000 units of heparin or other appropriate anticoagulant should be drawn into the syringe.

2. The syringe is then positioned with its needle pointed vertically upward so as to allow the blood to sediment (1xg) for 30-45 minutes. During sedimentation, the RBCs settle to the bottom of the syringe toward the plunger while leucocyte rich plasma remains at the top of the syringe proximate to the needle. In an alternative embodiment, sedimentation of the RBCs may be accelerated by the addition of Hespan (TM) (from 6% up to 20% hetastarch in 0.9% sodium chloride, DuPont, Del.).

3. The leucocyte rich plasma is then expressed from the syringe into a first centrifuge tube, preferrably a conventional 50 milliliter disposable centrifuge tube having a conical bottom and a composition of polypropylene. The leucocyte rich plasma is then centrifuged at 450xg for 7 minutes in order to pellet the leucocytes while forming a supernatant of platlet rich plasma (PRP).

4. The PRP supernatant is then withdrawn from the first centrifuge tube and transferred to a second centrifuge tube. The second centrifuge tube is then centrifuged at 950xg for 10 minutes to form platlet poor plasma (PPP). The PPP is then saved for use in steps 11 and 12 below.

5. In the meantime, the leucocyte pellet from the first centrifuge tube is resuspended in 4 milliliters of isotonic saline, i.e. 0.9% sodium chloride in sterile water for injection. Care should be taken when resuspending the leucocyte pellet not to swirl too vigorously so as to cause the formation of foam.

6. The first centrifuge tube containing the resuspended leucocytes is then mounted onto a rocker arm for separating residual RBCs from the leucocytes. The preferred rocker arm may be constructed by modifying a "Hema Tek" (TM) Aliquot Mixer, Model 4651, manufactured by the Ames Division of Miles Laboratories, Inc. (Elkhart, Ind.). The unmodified "Hema Tek" (TM) Aliquot Mixer consists of a tilting table, an actuating motor and a base. The platform tilts back and forth at 12 or 18 cycles per minute for mixing specimen samples. Other similar rocking devices may be obtained from Clay Adams (Nutator Mixer model #1105) and from American Scientific Products (American (TM) Tube Rocker catalog #R4185-10). Prior to modification, the tilting table cradles the specimen tubes in a horizontal position. In the preferred mode for constructing the rocker arm, the tilting table of the "Hema Tek" (TM) Aliquot Mixer is modified so as to securely brace one or more centrifuge tubes in a vertical position. When the rocker arm is activated, the centrifuge tubes oscillate around this vertical position. The motion of a single vertical centrifuge tube mounted upon the rocker arm is similar to that of a metronome which oscillates at 18 cycles per minute. The leucocyte suspension is allowed to rock upon the rocker arm for 15 minutes. During this rocking step, the leucocytes settle to the bottom of the centrifuge tube while the residual RBCs remain in the supernatant. The exact biochemical mechanism for this separation is unknown. It is speculated that the RBCs undergo a flocculation reaction or are otherwise hindered from settling with the leucocytes due to a surface charge phenomenon.

7. After rocking for 15 minutes, the rocker arm is stopped. The leucocytes are then depleted of residual RBCs by carefully removing and discarding the top 1 or 2 milliliters of supernatant. The volume of supernatant which is removed is then replaced with an equal volume of isotonic saline and the leucocytes are resuspended.

8. The resuspended leucocytes may then be rocked for 10 more minutes to separate out further residual RBCs. After 10 minutes, the rocker arm is again stopped. Again the rocking step has caused the leucocytes to settle to the bottom and the residual RBCs to remain within the supernatant. After the rocker arm has been stopped, the leucocytes would then be further depleted of residual RBCs by carefully removing the top 1 or 2 milliliters of supernatant.

9. The RBC depleted leucocytes of step 8 are then resuspended in 5.0 milliliters of isotonic saline and labelled by the addition of Indium In-111 oxine. Indium In-111 oxine (oxyquinoline solution) may be obtained from Amersham International, plc. (Amersham, Buckinghamshire, England). Each milliliter of the Amersham Indium In-111 oxyquinoline solution includes 1 millicurie of Indium In-111 at calibration, 50 micrograms of oxyquinoline, and 100 micrograms of polysorbate 80 in aqueous buffer. Indium In-111 has a half life of 2.8 days. An aliquot of 600 microcuries of the Amersham Indium In-111 oxyquinoline solution is then added to the resuspended leucocytes. The mixture of leucocytes and Indium In-111 solution is incubated for 15 minutes and swirled every 5 minutes.

10. After the 15 minute incubation, 1 milliliter of platelet poor plasma (PPP) is added to the labelled leucocytes as part of a wash step. The leucocytes and PPP are mixed by swirling. The leucocytes are then separated from unreacted Indium In-111 oxine by centrifugation at 450xg for 7 minutes. The supernatant is removed and discarded.

11. The washed pellet of labelled leucocytes is then resuspendend in platelet poor plasma (PPP) or saline solution (0.9% sodium chloride) to which 10% ACD solution may be added. The resuspended leucocytes should be injected into the patient as soon as possible, i.e. within 1 hour or not to exceed approximately 5 hours from time of the original blood collection.

The above protocol is merely exemplary of a perferred mode for practicing these aspects of the invention. For example, the protocol may be modified with good results by eliminating the second rocking step, i.e. step 8, and deleting the addition of isotonic saline in step 7.

The invention revolves around the preparation of the leucocyte sample for labelling with Indium In-111 oxine, i.e. the depletion of residual RBCs from the leucocytes (steps 5-8) prior to the labelling step. It is the addition of steps 5-8 which enables the labelling step (9) to achieve a significant enhancement of the leucocyte specific labelling efficiency and a significant decrease in tagged RBC contamination.

Comparative tests were performed for determining the relative enhancement of leucocyte specific labelling efficiency with and without the depletion steps (5-8). Samples from which RBCs had not been depleted included a significant contaminant of tagged RBCs, i.e. 20% of the Indium In-111 label was contained by contaminant RBCs. Samples from which RBCs had been depleted prior to Indium In-111 labelling were substantially without tagged RBC contaminant, i.e. 1-5% residual RBC contamination as measured by colorimetry.

What is claimed is:

1. An improved method for radio-labelling leucocytes with Indium In-111 oxine including the following steps:
   Step A: separating the leucocytes from whole blood for obtaining separated leucocytes mixed with residual red blood cells; and then
   Step B: labelling the separated leucocytes with Indium In-111 oxine;
   wherein the improvement comprises the following further step:
   Step A(1): after said Step A and prior to said Step B, depleting residual red blood cells from the separated leucocytes by resuspending the leucocytes in an isotonic saline solution, then rocking the resuspended leucocytes for causing the leucocytes to preferentially settle out, and then removing residual red blood cells which remain suspended within the supernatant isotonic saline solution.

2. An improved method for radio-labelling leucocytes as described in claim 1 wherein the improvement comprises the following further step:
   Step A(2): after said Step A(1) and prior to said Step B, further depleting residual red blood cells from the leucocytes by again resuspending the settled leucocytes in isotonic saline solution, then rocking the resuspended leucocytes for causing the leucocytes to preferentially settle out, and then removing residual red blood cells which remain suspended within the supernatant isotonic saline solution.

* * * * *